(12) United States Patent
Arimoto et al.

(10) Patent No.: US 7,297,349 B2
(45) Date of Patent: Nov. 20, 2007

(54) COPPER-CONTAINING FORMULATION FOR PLANT DISEASE CONTROL

(75) Inventors: Yutaka Arimoto, Saitama (JP); Akiko Hagiwara, Tokyo (JP); Kiyoshi Uchida, Ibaraki (JP); Yoshifumi Ota, Tokyo (JP)

(73) Assignees: Riken, Wako-shi (JP); Otsuka Chemical Co., Ltd, Osaka (JP)

( * ) Notice: Subject to any disclaimer, the term of this patent is extended or adjusted under 35 U.S.C. 154(b) by 44 days.

(21) Appl. No.: 11/066,217

(22) Filed: Feb. 28, 2005

(65) Prior Publication Data
US 2005/0170017 A1    Aug. 4, 2005

Related U.S. Application Data

(63) Continuation of application No. PCT/JP03/10793, filed on Aug. 26, 2003.

(30) Foreign Application Priority Data
Aug. 26, 2002 (JP) .............................. 2002-244743

(51) Int. Cl.
*A01N 59/20* (2006.01)
*A01N 59/26* (2006.01)
*A01N 25/32* (2006.01)

(52) U.S. Cl. ............... 424/606; 424/601; 424/602; 424/603; 424/604; 424/630; 424/632; 424/633; 424/634; 424/635; 424/637; 424/638; 514/499; 514/500

(58) Field of Classification Search ............... 424/603, 424/604, 606, 630, 637
See application file for complete search history.

(56) References Cited

U.S. PATENT DOCUMENTS

| 2,657,178 A | 10/1953 | Robinson, Jr. |
| 3,976,594 A * | 8/1976 | Dahlgren ................. 252/400.2 |
| 4,906,462 A | 3/1990 | Miki et al. |

FOREIGN PATENT DOCUMENTS

| EP | 640284 | 3/1995 |
| EP | 0 752 484 A1 | 1/1997 |
| EP | 0 891 711 A1 | 1/1999 |
| GB | 2 264 717 A | 9/1993 |
| JP | 60-260506 | 12/1985 |
| JP | 2-96508 | 4/1990 |
| JP | 8-3009 | 1/1996 |
| JP | 10-158101 | 6/1998 |

OTHER PUBLICATIONS

Derwent abstract 2000-673181; abstracting CN 1266037 (Sep. 2000).*
Patent Abstracts of Japan, JP 04072086, Mar. 6, 1992.
* cited by examiner

*Primary Examiner*—John Pak
(74) *Attorney, Agent, or Firm*—Oblon, Spivak, McClelland, Maier & Neustadt, P.C.

(57) ABSTRACT

The present invention relates to a copper-containing formulation for plant disease-control which comprises divalent copper and polyphosphate residues, wherein the amount of the polyphosphate residues per one chemical equivalent of the divalent copper is higher than one chemical equivalent. The copper-containing formulation of the present invention shows an excellent disease-control effect without causing any chemical injury of the plant.

30 Claims, No Drawings

COPPER-CONTAINING FORMULATION FOR PLANT DISEASE CONTROL

CROSS-REFERENCE TO A RELATED APPLICATION

The present application is a continuation of International Application PCT/JP03/10793 filed on Aug. 26, 2003, which claims priority to Japanese Patent Application No. 2002-244743, filed Aug. 26, 2002.

TECHNICAL FIELD

The present invention relates to a copper-containing formulation for plant disease control.

BACKGROUND ART

Copper sulfate generates copper ions in an aqueous solution thereof and shows a very strong bactericidal action or effect. Therefore, it has been used as an agricultural chemical over not less than 100 years, while making use of the foregoing characteristic properties. However, the copper ion likewise has a strong action of causing damage from agricultural chemicals (a phytotoxicity or a chemical injury) on a plant body. For this reason, there have been proposed a variety of means to use the same while masking the most use of the strong bactericidal action thereof and preventing any adverse effect thereof on the plant body. An example thereof is to mix copper sulfate with quick lime and the mixture has long been known as Bordeaux mixture and has been put in practical use. In this respect, however, the influence of the copper may vary depending on the kinds of plants. Accordingly, not only it would be necessary to change the mixing ratio of copper sulfate and quick lime for every particular plants, but also a technology of a high level would be required for the preparation of each particular mixture.

To this end, there has been designed the so-called premix Bordeaux. In this premix, a basic copper chloride or a basic copper sulfate is substituted for copper sulfate to thus inhibit any release of copper ions from the same. However, copper ions are rapidly released out of the premix due to, for instance, rainwater and this may give rise to damages from the agricultural chemical, in most of cases, even when using such premix Bordeaux. For this reason, calcium carbonate (such as a product sold under the trade name of kurefunon (calcium carbonate content: 95%)) is added to a spraying solution to further increase the basicity thereof and to thus prevent any release of copper ions from the premix. However, it is difficult to completely prevent the occurrence of any damage from agricultural chemicals even if the basicity of the premix is thus increased due to, for instance, a rainfall immediately after the spray of the same. In such a formulation, the release of copper ions is prevented by making the formulation basic and therefore, if the formulation is acidified by, for instance, acid rain, a large quantity of copper ions are released from the same and this would in turn lead to the occurrence of any damage from agricultural chemicals.

As has been discussed above, any conventional copper-containing formulations have been made strongly basic to thus prevent any release of copper ions for fear that any damage from agricultural chemicals may occur. Accordingly, in order to achieve or ensure a desired plant disease control effect, such a formulation should be sprayed on plants in a large quantity on the order of, for instance, 5 kg/ha. If a copper-containing formulation has been sprayed thereon over a long period of time, copper may accumulated in the soil and the release of the copper accumulated in the soil would cause the pollution of watercourses and drinking water.

When copper sulfate is mixed with sodium pyrophosphate or potassium pyrophosphate in water in a molar ratio of 2:1, copper pyrophosphate is formed, which is hardly soluble in water. Thus, the copper pyrophosphate is hardly soluble in water and therefore, it has never been used as an active component for an agricultural chemical. Moreover, it has been known that the copper pyrophosphate may be converted into a water-soluble one through the formation of a double salt or a complex salt with sodium pyrophosphate. Up to this time, however, there has not been any report concerning the bactericidal activity of this reaction product against vegetable pathogenic bacteria and/or fungi.

Japanese Un-Examined Patent Publication (hereunder referred to as "J.P. KOKAI") Hei 8-165213 discloses the effect of copper metaphosphate on *Escherichia coli*. In this respect, however, the copper metaphosphate is one prepared by heating ammonium dihydrogen phosphate and copper oxide at 800° C. and therefore, it comprises meta-phosphoric acid and copper in amounts of equal chemical equivalents.

J.P. KOKAI Hei 6-40806 discloses a bactericidal and insecticide composition containing a coated agricultural chemical prepared by coating 100 pars by mass of an effective component for the agricultural chemical with 0.1 to 10 parts by mass of a fatty acid ester of an aliphatic polyhydric alcohol and/or a phospholipids and 0.01 to 10 parts by mass of a pasting or sizing agent. As such a component for the agricultural chemical, there is listed, for instance, copper sulfate and examples of such pasting agents disclosed therein are sodium polyphosphate, potassium polyphosphate and sodium metaphosphate, but the mixing ratio of copper sulfate to, for instance, sodium polyphosphate is quite low and more specifically, the mixing rate of copper sulfate and, for instance, sodium polyphosphate is 0.01 to 10 parts by mass of the latter relative to 100 parts by mass of the former.

DISCLOSURE OF THE INVENTION

It is an object of the present invention to provide a copper-containing formulation for plant disease control, which has an excellent plant disease controlling effect without being accompanied by any damages from the agricultural chemical (any chemical injury).

The inventors of this invention added 2.0 moles of copper sulfate and more than 1.0 mole of sodium pyrophosphate (in a chemical equivalent ratio of higher than 1:1) to water and examined the activity of the resulting liquid against plant pathogenic bacteria and/or fungi without any post-treatment. As a result, they have found that the bactericidal effect thereof is quite high, that the risk of causing damages from agricultural chemical is considerably reduced and that the liquid can inhibit the occurrence of any disease injury due to mould against which the conventional inorganic copper-containing formulations do not show any control activity.

The present invention has been completed on the basis of the foregoing findings and accordingly, the present invention herein provides the following copper-containing formulations for plant disease control:

1. A copper-containing formulation for plant disease control comprising divalent copper and polyphosphate residues, wherein the amount of the polyphosphate residues per one chemical equivalent of the divalent copper is higher than one chemical equivalent.

2. The copper-containing formulation for plant disease control as set forth in the foregoing item 1, wherein the polyphosphate residue is at least one member selected from the group consisting of pyrophosphate residues, tripolyphosphate residues, tetrapolyphosphate residues, trimetaphosphate residues, and tetrametaphosphate residues.
3. The copper-containing formulation for plant disease control as set forth in the foregoing item 1 or 2, wherein the counter ions for the polyphosphate residues are alkali metal ions.
4. The copper-containing formulation for plant disease control as set forth in any one of the foregoing items 1 to 3, wherein the amount of the polyphosphate residues per one chemical equivalent of the divalent copper is higher than one chemical equivalent and not more than 4 chemical equivalents.
5. The copper-containing formulation for plant disease control as set forth in any one of the foregoing items 1 to 4, wherein it comprises copper sulfate and an alkali metal salt of polyphosphoric acid.
6. The copper-containing formulation for plant disease control as set forth in any one of the foregoing items 1 to 5, wherein it further comprises a surfactant.
7. The copper-containing formulation for plant disease control as set forth in the foregoing item 6, wherein the surfactant is at least one member selected from the group consisting of amphoteric surfactants, nonionic surfactants, and anionic surfactants.
8. The copper-containing formulation for plant disease control as set forth in the foregoing item 6, wherein the surfactant is an amphoteric surfactant.
9. The copper-containing formulation for plant disease control as set forth in the foregoing item 6, wherein the amphoteric surfactant is at least one member selected from the group consisting of polyoctyl polyaminoethyl glycine, alkyl polyaminoethyl glycine hydrochloride, and 2-alkyl-N-carboxymethyl-N-hydroxyethyl imidazolium betaine.
10. The copper-containing formulation for plant disease control as set forth in any one of the foregoing items 6 to 9, wherein the amount of the surfactant to be used ranges from 0.005 to 20 parts by mass per one part by mass of the copper compound.
11. The copper-containing formulation for plant disease control as set forth in any one of the foregoing items 1 to 10, wherein the plant disease injury is late blight of tomato, leaf mold of tomato, downy mildew of tomato, downy mildew of cucumber, anthracnose of cucumber, powdery mildew of cucumber, scab of pear, black spot of pear, fruit spot of apple, blotch of apple, angular and/or circular leaf spot of persimmon, anthracnose of persimmon, anthracnose of grape, leaf spot of grape, ripe rot of grape, downy mildew of grape, scab of orange, melanose of citrus fruits, melanose of orange, anthracnose of watermelon, downy mildew of cabbage, *Sclerotinia* rot of cabbage, late blight of potato, downy mildew of common onion, or *Alternaria* leaf spot of common onion.

BEST MODE FOR CARRYING OUT THE INVENTION

The conventional copper-containing formulations have been investigated such that the solubility thereof in water is reduced for fear of excess release of copper ions therefrom. For this reason, the copper-containing formulation has been basified. However, when the formulation is acidified, excess copper ions are easily dissolved out of or released from the formulation and accordingly, the occurrence of chemical injuries cannot be avoided. The inventors of this invention have thus conducted studies to develop a formulation having a composition essentially free of any excess release of copper ions and as a result, have found that the foregoing object of the present invention can be accomplished by a copper-containing formulation for plant disease control comprising divalent copper and polyphosphate residues in an amount of higher than one chemical equivalent per one chemical equivalent of the divalent copper.

Examples of divalent copper-containing compounds used in the copper-containing formulation according to the present invention include copper sulfate, copper chloride, copper nitrate, copper acetate and copper polyphosphate, with copper sulfate being particularly preferred. These copper-containing compounds may be those having water of crystallization or anhydrous ones.

Examples of polyphosphate residues used in the copper-containing formulation of the present invention include pyrophosphate residues, tripolyphosphate residues, tetrapolyphosphate residues, tri-metaphosphate residues, tetrametaphosphate residues, hexametaphosphate residues and mixtures comprising at least two kinds thereof. Among these, more preferably used herein are pyrophosphate residues, tripolyphosphate residues and tetrapolyphosphate residues. Examples of counter ions for the polyphosphate residues preferably used herein are alkali metal ions, with sodium or potassium ions being more preferred. In this respect, the combination of the foregoing polyphosphate residue and the counter ion thereof is herein also referred to as "polyphosphoric acid salt".

The present invention relates to a copper-containing formulation comprising divalent copper and polyphosphate residues, which is characterized in that the amount of the polyphosphate residues per one chemical equivalent of the divalent copper is higher than one chemical equivalent and preferably higher than one chemical equivalent and not more than 4 chemical equivalents. This is because if the amount of the polyphosphate residues is not more than one chemical equivalent per one chemical equivalent of the divalent copper, the resulting formulation may be liable to cause damage from agricultural chemical, while if it exceeds 4 chemical equivalent, the resulting formulation may be liable to show a reduced plant disease control effect. The alkali metal salt of polyphosphoric acid added to the copper-containing formulation according to the present invention may have an action of controlling the release of copper ions from the formulation.

In this connection, the chemical equivalents of the foregoing components will be described below with reference to the following chemical formula:

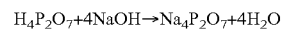

$$H_4P_2O_7 + 4NaOH \rightarrow Na_4P_2O_7 + 4H_2O$$

One mole of pyrophosphoric acid reacts with 4 moles of sodium hydroxide to give one mole of sodium pyrophosphate and 4 moles of water. More specifically, the amount of pyrophosphate residues present in one mole of pyrophosphoric acid corresponds to 4 chemical equivalents since the ionic valence of a pyrophosphate residue is 4, while that of sodium residue or ion present in one mole of sodium hydroxide corresponds to one chemical equivalent since the ionic valence of sodium ion is 1. Accordingly, the chemical equivalent of, for instance, divalent copper and tetravalent polyphosphate residue can be calculated from the ionic valence thereof. In other words, one mole of divalent copper ($Cu^{2+}$) is equal to 2 chemical equivalent and one mole of pyrophosphate residue corresponds to 4 chemical equivalents since the ionic valence of the pyrophosphate residue ($P_2O_7^{-4}$) is 4.

The following are preferred embodiments of the copper-containing formulations of the present invention.

A copper-containing formulation for plant disease control comprises copper sulfate and sodium or potassium pyrophosphate in which the mixing ratio thereof as expressed in terms of the molar ratio is such that the amount of the pyrophosphate preferably ranges from 1.01 to 4.0, more preferably 1.01 to 3.0 and most preferably 1.05 to 2.2 per 2.0 moles of copper sulfate.

A copper-containing formulation for plant disease control comprises copper sulfate and sodium or potassium tripolyphosphate in which the mixing ratio thereof as expressed in terms of the molar ratio is such that the amount of the tripolyphosphate preferably ranges from 1.01 to 4.0, more preferably 1.01 to 3.0 and most preferably 1.05 to 2.7 per 2.5 moles of copper sulfate.

A copper-containing formulation for plant disease control comprises copper sulfate and sodium or potassium tetrapolyphosphate in which the mixing ratio thereof as expressed in terms of the molar ratio is such that the amount of the tetrapolyphosphate preferably ranges from 1.01 to 4.0, more preferably 1.01 to 3.0 and most preferably 1.05 to 3.2 per 3.0 moles of copper sulfate.

A copper-containing formulation for plant disease control comprises copper sulfate and sodium or potassium tetrametaphosphate in which the mixing ratio thereof as expressed in terms of the molar ratio is such that the amount of the tripolyphosphate preferably ranges from 1.01 to 4.0, more preferably 1.01 to 3.0 and most preferably 1.05 to 2.0 per 2.0 moles of copper sulfate.

When the polyphosphate used is one having a distribution in its polymerization degree such as sodium hexametaphosphate (for instance, Graham's salt), the molecular formula thereof is assumed to be $(NaPO_3)_n$ and the molecular weight thereof is thus defined to be 102. For this reason, in the copper-containing formulation for plant disease control comprising copper sulfate and sodium hexametaphosphate, the latter is incorporated into the formulation in an amount of higher than 204 g, preferably ranging from 214 to 408 g and more preferably 214 to 306 g per 1.0 mole of copper sulfate.

The copper-containing formulation for plant disease control according to the present invention may further comprise, in addition to the foregoing copper-containing compound and polyphosphoric acid salt, at least one additive commonly used in a formulation when putting it into practical use as an agricultural chemical selected from the group consisting of, for instance, a surfactant [for instance, a nonionic surfactant (such as a linear alkyl polyoxyethylene ether and a polyoxyethylene castor oil), an anionic surfactant (such as an alkane sulfonic acid salt and an alkene sulfonic acid salt), a cationic surfactant (such as a dialkyl-dimethyl ammonium chloride and a benzalkonium salt), an amphoteric surfactant (such as a sulfo-betaine), a glycerin fatty acid ester (such as fatty acid monoglyceride), and a propylene glycol fatty acid ester], and a dispersant [for instance, synthetic silica (such as CARPLEX available from Shionogi & Co., Ltd. and NIPSEAL NS-T available from Nippon Silica Industries, Ltd.), and a mineral carrier such as kaolin, diatomaceous earth, talc and bentonite].

Such surfactants preferably used herein include, for instance, amphoteric surfactants, nonionic surfactants and anionic surfactant and specific examples thereof are amphoteric surfactants, for instance, polyoctyl polyaminoethyl glycine (such as a product available from Toho Chemical Industry Co., Ltd. under the trade name of OVAZOLINE B (containing 60% by mass of an effective component)), alkyl polyaminoethyl glycine hydrochlorides (such as a product available from Sanyo Chemical Industries, Ltd. under the trade name of LEVON U (containing 50% by mass of an effective component)), 2-alkyl-N-carboxymethyl-N-hydroxyethyl imidazolium betaines (such as a product available from Toho Chemical Industry Co., Ltd. under the trade name of OVAZOLINE 552 (containing 50% by mass of an effective component)); nonionic surfactants, for instance, glycerin monopalmitate; and anionic surfactants, for instance, sodium alkenyl-sulfonates (such as a product available from Toho Chemical Industry Co., Ltd. under the trade name of SOLPOL 5115). Preferably used herein as such surfactants further include, for instance, amphoteric surfactants and specific examples thereof include polyoctyl polyaminoethyl glycine, alkyl polyaminoethyl glycine hydrochlorides, and 2-alkyl-N-carboxymethyl-N-hydroxyethyl imidazolium betaines, with polyoctyl polyaminoethyl glycine and alkyl polyaminoethyl glycine hydrochlorides being particularly preferred.

The amount of these surfactants used herein ranges from 0.005 to 20 parts by mass, more preferably 0.01 to 10 parts by mass and particularly preferably 0.02 to 5 parts by mass per one part by mass of the copper-containing compound. The amounts of other additives in general range from about 0.01 to about 2.5 parts by mass per one part by mass of the copper-containing compound.

The present invention will hereunder be described in more detail with reference to copper-containing formulations for plant disease control each comprising copper sulfate and sodium pyrophosphate by way of example, but the present invention is not restricted to these specific examples at all.

Copper pyrophosphate is formed in an aqueous solution containing copper sulfate and sodium pyrophosphate in a mixing ratio of 2:1. This copper pyrophosphate is a quite stable compound and it has been reported that the solubility thereof in water is about $10^{-5}$ M. However, this compound has a high solubility in an acidic solution and a large amount of copper ions are released from the compound into the solution.

On the other hand, when mixing copper sulfate and sodium pyrophosphate in such a mixing rate of higher than one mole of the latter per 2 moles of the former, the amount of pyrophosphate ions relative to that of divalent copper ions increases in the resulting solution and it is considered that the pyrophosphate ions are partially converted into copper sodium pyrophosphate and/or copper hydrogen pyrophosphate.

As has been discussed above, in a solution in which copper sulfate and sodium pyrophosphate are mixed together in such a mixing rate of higher than one mole of the latter relative to 2 moles of the former, it is considered that a complicated equilibrium relation is established between, for instance, copper pyrophosphate, sodium pyrophosphate, copper ions, sodium ions, pyrophosphate ions, copper sodium pyrophosphate and copper hydrogen pyrophosphate. This is considered to be the reason why a damage from agricultural chemical is caused by a copper-containing formulation which comprises not more than one mole of sodium pyrophosphate relative to 2 moles of copper sulfate, while a higher plant disease control effect can be ensured, without causing any chemical injury, when using a copper-containing formulation which comprises higher than one mole of sodium pyrophosphate relative to 2 moles of copper sulfate.

The divalent copper ion has a high ability of linking with other compounds and it can easily be linked with, for instance, an amino acid adhered to the surface of a plant body to thus lose its activity of controlling plant disease. Moreover, if it reaches the interior of a plant body, it can link with a variety of plant components and thus becomes a cause of any damage from agricultural chemical.

Since the copper-containing formulation of the present invention has a considerably low ability of damaging a plant body and a considerably high effect of controlling plant disease and it is effective for a large number of plant diseases, it is suggested that the formulation shows a high ability of transferring into plant pathogens. Moreover, in case of the copper-containing formulation currently used as an agricultural chemical, the copper ion concentration thereof is small under the alkaline conditions, but it becomes high under acidic conditions and this would lead to the occurrence of damage from agricultural chemical. On the other hand, in case of the copper-containing formulation of the present invention, the copper ion concentration thereof undergoes a quite small change even when the pH value of the solution is changed and therefore, the formulation of the present invention has a quite low probability of causing chemical injuries.

The foregoing is not a phenomenon peculiar to the combination of copper sulfate and sodium pyrophosphate and this is a phenomenon also observed even for the foregoing combinations of other polyphosphoric acid compounds with copper sulfate or other copper-containing compound.

The copper-containing formulation of the present invention is in general used in the form of an aqueous solution and the pH value of this aqueous solution preferably ranges from 4.5 to 8.0 and more preferably 5.0 to 7.5.

It is suitable that the copper concentration of the copper-containing formulation upon the spray thereof preferably ranges from 20 to 2000 mg/L and more preferably 35 to 500 mg/L.

The copper-containing formulation of the present invention shows disease-preventing and disease-treating effects and is effective not only for the plant disease injuries due to bacteria, but also plant disease injuries due to fungi (mould). Moreover, the formulation of the invention may likewise be used as a disinfectant for seeds such as those of crops, for instance, wheat and barley and pulses; those of vegetables such as cucumber, tomato, lettuce and spinach; those of flowers such as pansy and morning glories; and those of rootcrops such as potato. Accordingly, the copper-containing formulation of the present invention also includes seed's disinfectant.

Examples of plant disease injuries to which the copper-containing formulation according to the present invention can effectively be applied include late blight of tomato, leaf mold of tomato, downy mildew of tomato, downy mildew of cucumber, anthracnose of cucumber, powdery mildew of cucumber, scab of pear, black spot of pear, fruit spot of apple, blotch of apple, angular and/or circular leaf spot of persimmon, anthracnose of persimmon, anthracnose of grape, leaf spot of grape, ripe rot of grape, downy mildew of grape, scab of orange, melanose of citrus fruits, melanose of orange, anthracnose of watermelon, downy mildew of cabbage, *Sclerotinia* rot of cabbage, late blight of potato, downy mildew of common onion, or *Alternaria* leaf spot of common onion.

The dosage form of the copper-containing formulation according to the present invention is preferably a water dispersible powder and it is converted into an aqueous solution upon its practical use. In this respect, it is preferred to prepare such an aqueous solution using a spreader or a wetting agent. Such a spreader used at this stage may be any one insofar as it can be used in the copper-containing formulation and specific examples thereof are polyoxyethylene alkyl ethers (for instance, a product available from Hokko Chemical Industry Co., Ltd. under the trade name of HYTEN A) and polyoxyethylene resin acids (for instance, a product available from Nippon Noyaku Co., Ltd. under the trade name of SPRAYSTICKER).

The sites of plants to be sprayed with the copper-containing formulation according to the present invention are above-ground parts of the plants and the formulation is sprayed on the sites during the growing season and dormant stage.

The amount of the formulation to be sprayed preferably ranges from 0.01 to 5 kg/ha and more preferably 0.2 to 1 kg/ha as expressed in terms of the amount of copper present therein.

The present invention will hereunder be described in more specifically with reference to the following Examples.

EXAMPLE 1

To copper sulfate, there was added potassium pyrophosphate in an amount of 0.8, 0.9, 1.0, 1.05, 1.1, 1.2, 1.4, 1.6, 1.8, 2.0, 2.2 or 2.4 moles per 2.0 moles of the copper sulfate and these components were sufficiently admixed together using a stirring machine.

EXAMPLE 2

To copper sulfate, there was added sodium pyrophosphate in an amount of 0.8, 0.9, 1.0, 1.05, 1.1, 1.2, 1.4, 1.6, 1.8, 2.0, 2.2 or 2.4 moles per 2.0 moles of the copper sulfate and these components were sufficiently admixed together using a stirring machine.

EXAMPLE 3

To copper sulfate, there was added sodium tripolyphosphate in an amount of 0.8, 0.9, 1.0, 1.05, 1.1, 1.2, 1.5, 2.0, 2.3, 2.5, 2.7 or 2.4 moles per 2.5 moles of the copper sulfate and these components were sufficiently admixed together using a stirring machine.

EXAMPLE 4

To copper sulfate, there was added potassium tripolyphosphate in an amount of 0.8, 0.9, 1.0, 1.05, 1.1, 1.2, 1.5, 2.0, 2.5, 3.0, 3.2 or 3.5 moles per 3.0 moles of the copper sulfate and these components were sufficiently admixed together using a stirring machine.

TEST EXAMPLE 1

Test for Disease Prevention Effects

Each of the copper-containing formulations prepared in Examples 1 to 4 was diluted with water so that the concentration thereof was equal to 6 mg/100 ml as expressed in terms of the amount of copper to thus prepare each corresponding test solution. This solution of an agricultural chemical was sprayed on the leaves of a plant, spores of a pathogenic fungus (zoospores) were inoculated through the spray thereof after drying the solution and then the plant was kept in a moist chamber (maintained at a temperature of 20° C. for late blight of tomato and downy mildew of cucumber, or 25° C. for anthracnose of cucumber or melanose of citrus fruits, and a humidity of 100%). Then the number of lesions generated was determined after 3 days from the inoculation for the late blight of tomato and the downy mildew of cucumber, after 4 days from the inoculation for the anthracnose of cucumber and after 5 days from the inoculation for the melanose of citrus fruits and the results thus obtained were compared with those observed for the control (a group free of any treatment with the foregoing agricultural solutions) to thus calculate each preventive value. In case of powdery mildew of cucumber, each test solution obtained by diluting each formulation to the foregoing concentration was sprayed on the leaves of cucumber seedlings, on which lesions had been formed, followed by the maintenance thereof at 25° C. and the determination of the number of lesions after 10 days to thus determine the preventive value.

Preventive Value (%) =[1−(number of lesions observed for each treated group)/(number of lesions observed for the control group)]×100

The following Table 1 shows the results observed in the foregoing test for controlling a variety of plant disease injuries obtained using the formulation prepared in Example 1; the following Table 2 shows the results observed in the foregoing test for controlling a variety of plant disease injuries obtained using the formulation prepared in Example 2; the following Table 3 shows the results observed in the foregoing test for controlling a variety of plant disease injuries obtained using the formulation prepared in Example 3; and the following Table 4 shows the results observed in the foregoing test for controlling a variety of plant disease injuries obtained using the formulation prepared in Example 4.

In the following Tables, the disease injuries to which the test solutions are applied (disease injuries tested) are as follows:

1: late blight of tomato; 2: downy mildew of cucumber; 3: anthracnose of cucumber; 4: melanose of citrus fruits; 5: powdery mildew of cucumber.

TABLE 1

| Ex. 1: $CuSO_4$/ | Disease Injuries Tested | | | | |
|---|---|---|---|---|---|
| $K_4P_2O_7$ | 1 | 2 | 3 | 4 | 5 |
| 2.0:0.8 | 85+++ | 92+++ | 88+++ | 93+++ | 87+++ |
| 2.0:0.9 | 87+++ | 91+++ | 86+++ | 89+++ | 83+++ |
| 2.0:1.0 | 94++ | 94++ | 94++ | 91++ | 82++ |
| 2.0:1.05 | 98− | 97− | 99− | 95− | 97− |
| 2.0:1.1 | 100− | 100− | 100− | 99− | 99− |
| 2.0:1.2 | 100− | 100− | 98− | 99− | 100− |
| 2.0:1.4 | 98− | 96− | 97− | 95− | 97− |
| 2.0:1.6 | 92− | 94− | 97− | 93− | 96− |
| 2.0:1.8 | 98− | 97− | 98− | 99− | 100− |
| 2.0:2.0 | 98− | 96− | 98− | 96− | 97− |
| 2.0:2.2 | 97− | 95− | 98− | 93− | 97− |
| 2.0:2.4 | 91− | 93− | 89− | 92− | 90− |

TABLE 2

| Ex. 2: $CuSO_4$/ | Disease Injuries Tested | | | | |
|---|---|---|---|---|---|
| $Na_4P_2O_7$ | 1 | 2 | 3 | 4 | 5 |
| 2.0:0.8 | 67+++ | 54+++ | 48+++ | 66+++ | 23+++ |
| 2.0:0.9 | 85+++ | 60+++ | 48+++ | 78+++ | 45+++ |
| 2.0:1.0 | 90++ | 92++ | 78++ | 87++ | 90++ |

TABLE 2-continued

| Ex. 2: $CuSO_4$/ | Disease Injuries Tested | | | | |
|---|---|---|---|---|---|
| $Na_4P_2O_7$ | 1 | 2 | 3 | 4 | 5 |
| 2.0:1.05 | 99− | 98− | 95− | 99− | 99− |
| 2.0:1.1 | 99− | 100− | 100− | 97− | 99− |
| 2.0:1.2 | 97− | 94− | 96− | 92− | 97− |
| 2.0:1.4 | 95− | 93− | 99− | 92− | 90− |
| 2.0:1.6 | 94− | 92− | 91− | 94− | 97− |
| 2.0:1.8 | 95− | 98− | 92− | 97− | 94− |
| 2.0:2.0 | 100− | 100− | 99− | 99− | 100− |
| 2.0:2.2 | 94− | 97− | 98− | 94− | 96− |
| 2.0:2.4 | 89− | 87− | 82− | 94− | 91− |

TABLE 3

| Ex. 3: $CuSO_4$/ | Disease Injuries Tested | | | | |
|---|---|---|---|---|---|
| $Na_5P_3O_{10}$ | 1 | 2 | 3 | 4 | 5 |
| 2.5:0.8 | 78+++ | 49+++ | 50+++ | 58+++ | 46+++ |
| 2.5:0.9 | 79+++ | 58+++ | 53+++ | 66+++ | 60+++ |
| 2.5:1.0 | 86++ | 90++ | 78++ | 84++ | 77++ |
| 2.5:1.05 | 98− | 99− | 97− | 96− | 98− |
| 2.5:1.1 | 100− | 100− | 99− | 98− | 100− |
| 2.5:1.2 | 97− | 95− | 99− | 94− | 96− |
| 2.5:1.5 | 90− | 95− | 93− | 96− | 93− |
| 2.5:2.0 | 94− | 96− | 93− | 92− | 96− |
| 2.5:2.3 | 96− | 98− | 94− | 99− | 94− |
| 2.5:2.5 | 99− | 99− | 98− | 100− | 100− |
| 2.5:2.7 | 96− | 94− | 92− | 94− | 95− |
| 2.5:3.0 | 89− | 86− | 90− | 85− | 80− |

TABLE 4

| Ex. 4: $CuSO_4$/ | Disease Injuries Tested | | | | |
|---|---|---|---|---|---|
| $K_6P_4O_{13}$ | 1 | 2 | 3 | 4 | 5 |
| 3.0:0.8 | 66+++ | 45+++ | 64+++ | 74+++ | 44+++ |
| 3.0:0.9 | 70+++ | 62+++ | 74+++ | 78+++ | 57+++ |
| 3.0:1.0 | 88++ | 92++ | 87++ | 90++ | 91++ |
| 3.0:1.05 | 94− | 100− | 98− | 99− | 96− |
| 3.0:1.1 | 100− | 100− | 99− | 99− | 97− |
| 3.0:1.2 | 99− | 96− | 99− | 96− | 95− |
| 3.0:1.5 | 90− | 93− | 98− | 93− | 96− |
| 3.0:2.0 | 89− | 90− | 93− | 95− | 99− |
| 3.0:2.5 | 96− | 94− | 93− | 97− | 92− |
| 3.0:3.0 | 100− | 100− | 100− | 98− | 99− |
| 3.0:3.2 | 98− | 96− | 94− | 99− | 99− |
| 3.0:3.5 | 90− | 88− | 90− | 86− | 80− |

The symbol positioned behind each preventive value means the extent of the damage from each test solution (those appearing in the following Tables are the same as those used in the foregoing Tables also):

−: There is not observed any lesion due to phytotoxicity (no damage from each particular test solution);
+: There are observed a small number of lesions due to phytotoxicity;
++: There are observed a fairly large number of lesions due to phytotoxicity;
+++: There are observed a considerable number of lesions due to phytotoxicity.

Consideration of Results:

Regarding the compositions of the formulation used in Example 1, severe chemical injuries were observed for the test solutions each comprising copper sulfate and potassium pyrophosphate at a molar ratio of copper sulfate to potassium pyrophosphate ranging from 2.0:0.8 to 2.0:1.0. On the other hand, there was not observed any chemical injury for the test solutions each having such a molar ratio ranging from 2.0:1.05 to 2.0:2.4. There were observed excellent disease-control effects for the test solutions each having such a molar ratio ranging from 2.0:1.05 to 2.0:2.2.

Regarding the compositions of the formulation used in Example 2, severe chemical injuries were observed for the test solutions each comprising copper sulfate and sodium pyrophosphate at a molar ratio of copper sulfate to sodium pyrophosphate ranging from 2.0:0.8 to 2.0:1.0. On the other hand, there was not observed any chemical injury for the test solutions each having such a molar ratio ranging from 2.0:1.05 to 2.0:2.4. There were observed excellent disease-control effects for the test solutions each having such a molar ratio ranging from 2.0:1.05 to 2.0:2.2.

Regarding the compositions of the formulation used in Example 3, severe chemical injuries were observed for the test solutions each comprising copper sulfate and sodium tripolyphosphate at a molar ratio of copper sulfate to sodium tripolyphosphate ranging from 2.5:0.8 to 2.5:1.0. On the other hand, there was not observed any chemical injury for the test solutions each having such a molar ratio ranging from 2.5:1.05 to 2.5:3.0. There were observed excellent disease-control effects for the test solutions each having such a molar ratio ranging from 2.5:1.05 to 2.5:2.7.

Regarding the compositions of the formulation used in Example 4, severe chemical injuries were observed for the test solutions each comprising copper sulfate and potassium tetrapolyphosphate at a molar ratio of copper sulfate to potassium tetrapolyphosphate ranging from 3.0:0.8 to 3.0:1.0. On the other hand, there was not observed any chemical injury for the test solutions each having such a molar ratio ranging from 3.0:1.05 to 3.0:3.5. There were observed excellent disease-control effects for the test solutions each having such a molar ratio ranging from 3.0:1.05 to 3.0:3.2.

TEST EXAMPLE 2

Test for Disease Prevention Effects (Comparison with Z-Bordeaux Mixture and KOCIDE Bordeaux Mixture)

There were prepared test solutions, or the formulations prepared in Examples 1 and 2, whose molar ratio of copper sulfate to polyphosphoric acid were 2.0:1.1 and 2.0:2.0; those prepared from Z-Bordeaux Mixture (available from TOMONOAGRICA) and KOCIDE Bordeaux Mixture (available from Shionogi & Co., Ltd.) having practical spray concentrations and copper concentrations (6 mg/100 ml) identical to those of the formulations of Examples 1 and 2 having the foregoing molar ratio. Each test solution was sprayed on the seedlings of tomato, the seedlings were then inoculated with zoospores of the causal bacteria for late blight of tomato after the air-drying of the test solution, the seedlings were kept in a moist chamber maintained at 20° C. (having a humidity of 100%), and then the number of lesions formed on the leaves due to the disease was determined after 4 days from the inoculation to thus calculate the preventive value for each test solution. The results thus obtained are summarized in the following Tables 5 and 6:

TABLE 5

Test Result 1: Comparison of Effects and Chemical Injuries Observed at the Practical Concentrations

| Sample (Molar Ratio: Cu/Polyphosphoric acid) | Dilution Factor | Cu Concn. (mg/100 ml) | Preventive Value (%) | Chemical Injury |
|---|---|---|---|---|
| Ex. 1 (2:1.1) | ×2000 | 6 | 100 | – |
| Ex. 1 (2:2.0) | ×2000 | 6 | 98 | – |
| Ex. 2 (2:1.1) | ×2000 | 6 | 99 | – |
| Ex. 2 (2:2.0) | ×2000 | 6 | 99 | – |
| Z-Bordeaux Mixture | ×500 | 64 | 99 | ++ |
| KOCIDE Bordeaux Mixture | ×1000 | 50 | 100 | +++ |
| Free of Any Treatment | — | — | 0 | – |

TABLE 6

Test Result 2: Comparison of Effects and Chemical Injuries Observed at a copper concentration of 6 mg/100 ml

| Sample (Molar Ratio: Cu/Polyphosphoric acid) | Cu Concn. (mg/100 ml) | Preventive Value (%) | Chemical Injury |
|---|---|---|---|
| Ex. 1 (2:1.1) | 6 | 99 | – |
| Ex. 1 (2:2.0) | 6 | 98 | – |
| Ex. 2 (2:1.1) | 6 | 100 | – |
| Ex. 2 (2:2.0) | 6 | 99 | – |
| Z-Bordeaux Mixture | 6 | 28 | – |
| KOCIDE Bordeaux Mixture | 6 | 35 | – |
| Free of Any Treatment | – | 0 | – |

The data listed in Tables 5 and 6 indicate that the copper-containing formulation of the invention shows a high preventive value at a low concentration without causing any chemical damage, while Z-Bordeaux and KOCIDE Bordeaux mixtures should be used in high concentrations to achieve high preventive values and in this case, they cause chemical injuries. The data also indicate that, in the latter case, if they are used in low concentrations to prevent the occurrence of any chemical injury, they are not practical since the preventive values achieved at such low concentrations are too low.

The following Table 7 shows the copper contents, dilution factors and application doses of the formulations of Examples 1 and 2, and Z-Bordeaux and KOCIDE Bordeaux mixtures; and the copper concentrations observed when the concentrations of these samples are adjusted to corresponding application doses:

TABLE 7

| Sample (Molar Ratio: Cu/Poly⁻ phosphoric acid) | Cu Content (%) | Dilution Factor | Appln. Dose (mg/100 ml) | Cu Concn. (mg/100 ml) |
|---|---|---|---|---|
| Ex. 1 (2:1.1) | 12 | ×2000 | 50 | 6 |
| Ex. 1 (2:2.0) | 12 | ×2000 | 50 | 6 |
| Ex. 2 (2:1.1) | 12 | ×2000 | 50 | 6 |
| Ex. 2 (2:2.0) | 12 | ×2000 | 50 | 6 |
| Z-Bordeaux Mixture | 32 | ×500 | 640 | 64 |
| KOCIDE Bordeaux Mixture | 50 | ×1000 | 500 | 50 |

TEST EXAMPLE 3

Test for Chemical Injury of Agricultural Chemical Formulations with Respect to Various Kinds of Plants Test sample solutions of the present invention, and Z-Bordeaux and KOCIDE Bordeaux mixtures which had been diluted to predetermined concentrations were sprayed on seedlings of a variety of plants at copper concentrations specified in the following Table and the seedlings were kept in a moist chamber maintained at 20° C. (having a humidity of 100%). Then the degrees of chemical injuries generated on the leaves of the seedlings were compared with one another after a predetermined period of time (4 days). The results thus obtained are summarized in the following Table 8:

TABLE 8

| Sample | Cu Concn. (mg/100 ml) | Degree of Chemical Injury | | | |
|---|---|---|---|---|---|
| | | Tomato | Cucumber | Orange | Lettuce |
| Ex. 1 (2:1.1) | 6 | — | — | — | — |
| Ex. 1 (2:2.0) | 6 | — | — | — | — |
| Ex. 2 (2:1.1) | 6 | — | — | — | — |
| Ex. 2 (2:2.0) | 6 | — | — | — | — |
| Z-Bordeaux Mixture | 64 | ++ | + | ++ | +++ |
| KOCIDE Bordeaux Mixture | 50 | ++ | ++ | +++ | +++ |

As a result, it was found that there was not observed any chemical injury for the copper-containing formulations of the present invention, while Z-Bordeaux and KOCIDE Bordeaux mixtures caused severe chemical injuries.

EXAMPLES 5 TO 7

Copper-containing formulations were prepared according to the mixing ratios specified in the following Table 9. In this Table, the unit of each numerical value is part by mass.

TABLE 9

| | Example No. | | |
|---|---|---|---|
| | 5 | 6 | 7 |
| Copper Compound | | | |
| $CuSO_4$ | 36.9 | — | 33.1 |
| $CuSO_4 \cdot 5H_2O$ | — | 34.7 | — |
| Polyphosphoric acid salt | | | |
| $Na_4P_2O_7$ | 33.8 | — | 33.1 |
| $K_4P_2O_7$ | — | 29.7 | — |
| Surfactant | | | |
| C12~C14-Alkenylsulfonate (SOLPOL 5115) | 7.4 | — | — |
| Polyoxyethylene styryl-phenyl ether (SOLPOL 5080) | — | 4.9 | — |
| Sodium Naphthalene-sulfonate-formalin condensate (DEMOL N) | — | 1.0 | 0.1 |
| Propylene glycol mono-oleate (LIKEMAL P-100) | 1.0 | — | — |
| Dispersant | | | |
| White carbon (NIPSEAL NS-T) | 19.7 | — | — |
| Sodium benzoate | — | 29.7 | 33.1 |
| Clay (HIRAKI BP) | 1.2 | — | — |
| Kaolin | — | — | 0.6 |

TEST EXAMPLE 4

The abilities of the formulations prepared in Examples 5 to 7 to control late blight of tomato and downy mildew of cucumber were examined according to the method described above. The results thus obtained are summarized in the following Table 10.

TABLE 10

| | | Preventive Value (%) | |
|---|---|---|---|
| Sample | Cu Concn. (mg/100 ml) | late blight of tomato | downy mildew of cucumber |
| Ex. 5 | 6 | 100 | 100 |
| Ex. 5 | 4 | 88 | 92 |
| Ex. 6 | 6 | 98 | 96 |
| Ex. 6 | 4 | 81 | 87 |
| Ex. 7 | 6 | 97 | 95 |
| Ex. 7 | 4 | 83 | 92 |
| Z-Bordeaux | 64 | 100 | 99 |
| Z-Bordeaux | 42 | 72 | 68 |
| KOCIDE Bordeaux | 50 | 97 | 99 |
| KOCIDE Bordeaux | 33 | 65 | 76 |

EXAMPLE 8

There were sufficiently mixed 35.6% by mass of copper sulfate, 32.6% by mass of sodium pyrophosphate, 14.0% by mass of an amphoteric surfactant, 16.6% by mass of synthetic silica (white carbon) and 1.2% by mass of clay (HIRAKI BP) using a stirring machine to thus form a copper-containing formulation. In this respect, the amphoteric surfactant used was polyoctyl polyaminoethyl glycine (a product containing 60% by mass of this component and available from Toho Chemical Industry Co., Ltd. under the trade name of OVAZOLINE B).

EXAMPLE 9

There were sufficiently mixed 35.6% by mass of copper sulfate, 32.6% by mass of sodium pyrophosphate, 14.0% by mass of an amphoteric surfactant, 16.6% by mass of synthetic silica (white carbon) and 1.2% by mass of clay (HIRAKI BP) using a stirring machine to thus form a copper-containing formulation. In this respect, an alkyl polyaminoethyl glycine hydrochloride (a product containing 50% by mass of this component and available from Sanyo Chemical Industries, Ltd. under the trade name of LEBON U) was used herein as the amphoteric surfactant.

EXAMPLE 10

There were sufficiently mixed 35.6% by mass of copper sulfate, 32.6% by mass of sodium pyrophosphate, 30.6% by mass of synthetic silica (white carbon) and 1.2% by mass of clay (HIRAKI BP) using a stirring machine to thus form a copper-containing formulation.

EXAMPLE 11

There were sufficiently mixed 35.6% by mass of copper sulfate, 32.6% by mass of sodium pyrophosphate, 14.0% by mass of an amphoteric surfactant, 16.6% by mass of synthetic silica (white carbon) and 1.2% by mass of clay (HIRAKI BP) using a stirring machine to thus form a copper-containing formulation. In this respect, a 2-alkyl-N-carboxymethyl-N-hydroxyethyl-imidazolium betaine (a product containing 50% by mass of this component and available from Toho Chemical Industry Co., Ltd. under the trade name of OVAZOLINE 552) was used herein as the amphoteric surfactant.

EXAMPLE 12

There were sufficiently mixed 35.6% by mass of copper sulfate, 32.6% by mass of sodium pyrophosphate, 1.0% by mass of a nonionic surfactant, 29.6% by mass of synthetic silica (white carbon) and 1.2% by mass of clay (HIRAKI BP) using a stirring machine to thus form a copper-containing formulation. In this respect, glycerin monopalmitate was used herein as the nonionic surfactant.

EXAMPLE 13

There were sufficiently mixed 35.6% by mass of copper sulfate, 32.6% by mass of sodium pyrophosphate, 7.1% by mass of an anionic surfactant, 23.5% by mass of synthetic silica (white carbon) and 1.2% by mass of clay (HIRAKI BP) using a stirring machine to thus form a copper-containing formulation. In this respect, sodium alkenyl sulfonate (a product available from Toho Chemical Industry Co., Ltd. under the trade name of SOLPOL 5115) was used herein as the anionic surfactant.

TEST EXAMPLE 5

The copper-containing formulations prepared in Examples 8 to 10 were diluted with water to a concentration of 9 mg/100 ml as expressed in terms of the amount of copper to thus form solutions of agricultural chemicals (sample solutions) and the resulting samples were inspected for the degree of progression of lesions or downy mildew of cucumber. More specifically, each of these sample solutions was sprayed on the leaves of cucumber, spores of a causal fungus (zoospores) of this disease were inoculated through the spray thereof after drying the solution and then the plant was kept in a moist chamber (maintained at a temperature of 20° C. and a humidity of 100%). Thereafter, the score of lesions generated was determined. The results thus obtained are summarized in the following Table 13. The data shown in Table 13 indicate that the formulations of Examples 8 and 9 containing amphoteric surfactants incorporated into the same are superior in the degree of progression of lesions to the formulation of Example 10 free of any amphoteric surfactant.

TABLE 13

| Sample | Score of lesions determined after 5 days from the spore-inoculation |
|---|---|
| Copper-containing formulation of Ex. 8 | 2, 2, 3 |
| Copper-containing formulation of Ex. 9 | 1, 2, 2 |
| Copper-containing formulation of Ex. 10 | 4, 4, 4 |
| Free of any treatment (control) | 5, 5, 5 |

In Table 13, the evaluation standards for the score of lesions are as follows:
0: The area occupied by lesions is 0%;
1: The area occupied by lesions is not more than 25%;
2: The area occupied by lesions is more than 25% and not more than 50%;
3: The area occupied by lesions is more than 50% and not more than 75%;
4: The area occupied by lesions is more than 75% and less than 100%;
5: The area occupied by lesions is 100% (the entire leaves are completely withered).

TEST EXAMPLE 6

The copper-containing formulations prepared in Examples 10 to 13 were likewise inspected for the degree of progression of lesions or downy mildew of cucumber according to the procedures identical to those used in Test Example 5. As a result, it was found that the degree of progression of lesions was most strongly inhibited by the formulation of Example 11 which comprised an amphoteric surfactant incorporated therein. The inhibition of the degree of progression of lesions was likewise observed for the formulation prepared in Example 10, 12 or 13 as compared with that observed for the control.

TABLE 14

| Sample | Score of lesions determined after 5 days from the spore-inoculation |
|---|---|
| Copper-containing formulation of Ex. 10 | 3, 4 |
| Copper-containing formulation of Ex. 11 | 1, 1, 3 |
| Copper-containing formulation of Ex. 12 | 4, 4 |
| Copper-containing formulation of Ex. 13 | 3, 3, 4 |
| Free of any treatment (control) | 5, 5, 5 |

In Table 14, the evaluation standards for the score of lesions are the same as those used in Table 13.

INDUSTRIAL APPLICABILITY

The copper-containing formulation of the present invention shows a considerably low ability to cause chemical injury, has a considerably high disease-control effect and shows such a control effect on a quite wide range of diseases.

What is claimed is:

1. A copper-containing composition comprising:
   divalent copper,
   polyphosphate residue(s), and
   a surfactant;
   wherein the polyphosphate residue is at least one member selected from the group consisting of a pyrophosphate residue, tripolyphosphate residue, tetrapolyphosphate residue, trimetaphosphate residue, and tetrametaphosphate residue;
   wherein the amount of the polyphosphate residues per one chemical equivalent of the divalent copper is higher than one chemical equivalent and not more than 4 chemical equivalents;
   wherein the surfactant is at least one member selected from the group consisting of polyoctyl polyaminoethyl glycine, alkyl polyaminoethyl glycine hydrochlorides, and 2-alkyl-N-carboxymethyl-N-hydroxyethyl imidazolium betaine; or is at least one member selected from the group consisting of $C_{12-14}$-alkenylsulfonate, polyoxyethylene styryl-phenyl ether, sodium naphthalene sulfonate formalin condensate, propylene glycol monooleate, alkyl polyaminoethyl glycine hydrochloride, and 2-alkyl-N-carboxymethyl-N-hydroxyethyl-imidazolium betaine.

2. The composition of claim 1, wherein the polyphosphate residue is at least one member selected from the group consisting of a pyrophosphate residue, tripolyphosphate residue, and tetrapolyphosphate residue.

3. The composition of claim 1, wherein the counter ions for the polyphosphate residues are alkali metal ions.

4. The composition of claim 1,
   which comprises sodium or potassium pyrophosphate in a molar ratio of 1.05 to 2.2 per 2.0 moles of copper sulfate;

which comprises sodium or potassium tripolyphosphate in a molar ratio of 1.05 to 2.7 per 2.5 moles of copper sulfate;

which comprises sodium or potassium tetrapolyphosphate in a molar ratio of 1.05 to 3.2 per 3.0 moles of copper sulfate; or which comprises sodium or potassium tetrametaphosphate in a molar ratio of 1.05 to 2.0 per 2.0 moles of copper sulfate.

5. The composition of claim 1, which includes copper sulfate and an alkali metal salt of polyphosphoric acid.

6. The composition of claim 1, further comprising a dispersant.

7. The composition of claim 1, which has a pH ranging from 5.0 to 7.5 and a copper concentration ranging from 35 to 500 mg/L.

8. The composition of claim 1, wherein the surfactant is at least one member selected from the group consisting of polyoctyl polyaminoethyl glycine, alkyl polyaminoethyl glycine hydrochlorides, and 2-alkyl-N-carboxymethyl-N-hydroxyethyl imidazolium betaine.

9. The composition of claim 1, wherein the amount of the surfactant to be used ranges from 0.005 to 20 parts by mass per one part by mass of the copper compound.

10. The composition of claim 1 at a concentration and in an amount sufficient to treat a plant disease, wherein said disease is late blight of tomato, leaf mold of tomato, downy mildew of tomato, downy mildew of cucumber, anthracnose of cucumber, powdery mildew of cucumber, scab of pear, black spot of pear, fruit spot of apple, blotch of apple, angular and/or circular leaf spot of persimmon, anthracnose of persimmon, anthracnose of grape, leaf spot of grape, ripe rot of grape, downy mildew of grape, scab of orange, melanose of citrus fruits, melanose of orange, anthracnose of watermelon, downy mildew of cabbage, Sclerotinia rot of cabbage, late blight of potato, downy mildew of common onion, or Alternaria leaf spot of common onion.

11. The composition of claim 1, which includes copper sulfate and sodium or potassium pyrophosphate.

12. The composition of claim 11, wherein the surfactant is at least one member selected from the group consisting of $C_{12-14}$-alkenylsulfonate, polyoxyethylene styryl-phenyl ether, sodium naphthalene sulfonate formalin condensate, propylene glycol mono-oleate, alkyl polyaminoethyl glycine hydrochloride, and 2-alkyl-N-carboxymethyl-N-hydroxyethyl-imidazolium betaine.

13. The composition of claim 12, which further comprises at least one member selected from the group consisting of synthetic silica and clay.

14. The composition of claim 1, which includes:
copper sulfate,
sodium pyrophosphate,
at least one member selected from the group consisting of alkyl polyaminoethyl glycine hydrochloride, and 2-alkyl-N-carboxymethyl-N-hydroxyethyl-imidazolium betaine, and
at least one member selected from the group consisting of synthetic silica and clay.

15. A method for controlling plant disease, which comprises applying to a plant a copper-containing composition comprising:
divalent copper,
polyphosphate residue(s), and
a surfactant;
wherein the polyphosphate residue is at least one member selected from the group consisting of a pyrophosphate residue, tripolyphosphate residue, tetrapolyphosphate residue, trimetaphosphate residue, and tetrametaphosphate residue;

wherein the amount of the polyphosphate residues per one chemical equivalent of the divalent copper is higher than one chemical equivalent and not more than 4 chemical equivalents;

wherein the surfactant is at least one member selected from the group consisting of polyoctyl polyaminoethyl glycine, alkyl polyaminoethyl glycine hydrochlorides, and 2-alkyl-N-carboxymethyl-N-hydroxyethyl imidazolium betaine; or is at least one member selected from the group consisting of $C_{12-14}$-alkenylsulfonate, polyoxyethylene styryl-phenyl ether, sodium naphthalene sulfonate formalin condensate, propylene glycol mono-oleate, alkyl polyaminoethyl glycine hydrochloride, and 2-alkyl-N-carboxymethyl-N-hydroxyethyl-imidazolium betaine.

16. The method of claim 15, wherein in said composition the polyphosphate residue is at least one member selected from the group consisting of pyrophosphate residues, tripolyphosphate residues, and tetrapolyphosphate residues.

17. The method of claim 15, wherein in said composition the counter ions for the polyphosphate residues are alkali metal ions.

18. The method of claim 15, wherein said composition comprises:
sodium or potassium pyrophosphate in a molar ratio of 1.05 to 2.2 per 2.0 moles of copper sulfate;
sodium or potassium tripolyphosphate in a molar ratio of 1.05 to 2.7 per 2.5 moles of copper sulfate;
sodium or potassium tetrapolyphosphate in a molar ratio of 1.05 to 3.2 per 3.0 moles of copper sulfate; or
sodium or potassium tetrametaphosphate in a molar ratio of 1.05 to 2.0 per 2.0 moles of copper sulfate.

19. The method of claim 15, wherein said composition includes copper sulfate and an alkali metal salt of polyphosphoric acid.

20. The method of claim 15, wherein said composition further comprises a dispersant.

21. The method of claim 15, wherein said composition has a pH ranging from 5.0 to 7.5 and a copper concentration ranging from 35 to 500 mg/L.

22. The method of claim 15, wherein the surfactant in said composition is at least one member selected from the group consisting of polyoctyl polyaminoethyl glycine, alkyl polyaminoethyl glycine hydrochlorides, and 2-alkyl-N-carboxymethyl-N-hydroxyethyl imidazolium betaine.

23. The method of claim 15, wherein the amount of the surfactant in said composition ranges from 0.005 to 20 parts by mass per one part by mass of the copper compound.

24. The method of claim 15, wherein the plant disease is late blight of tomato, leaf mold of tomato, downy mildew of tomato, downy mildew of cucumber, anthracnose of cucumber, powdery mildew of cucumber, scab of pear, black spot of pear, fruit spot of apple, blotch of apple, angular and/or circular leaf spot of persimmon, anthracnose of persimmon, anthracnose of grape, leaf spot of grape, ripe rot of grape, downy mildew of grape, scab of orange, melanose of citrus fruits, melanose of orange, anthracnose of watermelon, downy mildew of cabbage, Sclerotinia rot of cabbage, late blight of potato, downy mildew of common onion, or Alternaria leaf spot of common onion.

25. The method of claim 15, wherein the composition is in the form of an aqueous solution having a pH of 4.5 to 8.0.

26. The method of claim 15, wherein the copper concentration in the composition upon the application to the plant ranges from 20 to 2,000 mg/L.

27. The method of claim 15, wherein said composition includes copper sulfate, and sodium or potassium pyrophosphate.

28. The method of claim 15, wherein in said composition the surfactant is at least one member selected from the group consisting of $C_{12-14}$-alkenylsulfonate, polyoxyethylene styryl-phenyl ether, sodium naphthalene sulfonate formalin condensate, propylene glycol mono-oleate, alkyl polyaminoethyl glycine hydrochloride, and 2-alkyl-N-carboxymethyl-N-hydroxyethyl-imidazolium betaine.

29. The method of claim 28, wherein said composition further comprises at least one member selected from the group consisting of synthetic silica and clay.

30. The method of claim 15, wherein said composition includes copper sulfate, sodium pyrophosphate, at least one member selected from the group consisting of alkyl polyaminoethyl glycine hydrochloride, and 2-alkyl-N-carboxymethyl-N-hydroxyethyl-imidazolium betaine, and at least one member selected from the group consisting of synthetic silica and clay.

* * * * *